(12) United States Patent
Dharmadhkari et al.

(10) Patent No.: US 9,439,851 B2
(45) Date of Patent: Sep. 13, 2016

(54) GASTRIC RETENTION SYSTEM

(75) Inventors: Nitin Bhalachandra Dharmadhkari, Mumbai (IN); Yashoraj Rupsinh Zala, Mumbai (IN)

(73) Assignee: SUN PHARMA ADVANCED RESEARCH COMPANY LTD., Andheri (East) (IN)

( * ) Notice: Subject to any disclaimer, the term of this patent is extended or adjusted under 35 U.S.C. 154(b) by 1672 days.

(21) Appl. No.: 10/593,816

(22) PCT Filed: Mar. 24, 2005

(86) PCT No.: PCT/IN2005/000091
§ 371 (c)(1),
(2), (4) Date: Sep. 7, 2007

(87) PCT Pub. No.: WO2005/101983
PCT Pub. Date: Nov. 3, 2005

(65) Prior Publication Data
US 2008/0107732 A1 May 8, 2008

(30) Foreign Application Priority Data

Mar. 25, 2004 (IN) ............ 364/MUM/2004
Oct. 7, 2004 (IN) ............ 1058/MUM/2004

(51) Int. Cl.
*A61K 9/00* (2006.01)
*A61F 5/00* (2006.01)
*A61K 9/24* (2006.01)
*A61K 9/28* (2006.01)
*A61K 9/48* (2006.01)

(52) U.S. Cl.
CPC ............ *A61K 9/0065* (2013.01); *A61F 5/003* (2013.01); *A61F 5/0036* (2013.01); *A61K 9/209* (2013.01); *A61K 9/2886* (2013.01); *A61K 9/4891* (2013.01)

(58) Field of Classification Search
CPC ... A61F 5/003; A61F 5/0036; A61K 9/4891; A61K 9/209; A61K 9/2886; A61K 9/0065
See application file for complete search history.

(56) References Cited

U.S. PATENT DOCUMENTS

| | | |
|---|---|---|
| 3,786,813 A | 1/1974 | Michaels |
| 4,101,650 A | 7/1978 | Umezawa |
| 4,207,890 A | 6/1980 | Mamajek et al. |
| 4,777,033 A | 10/1988 | Ikura et al. |
| 4,844,905 A | 7/1989 | Ichikawa et al. |
| 4,996,058 A | 2/1991 | Sinnreich |
| 5,380,533 A * | 1/1995 | Egidio et al. ............ 424/456 |
| 5,651,985 A | 7/1997 | Penners et al. |
| 5,783,212 A | 7/1998 | Fassihi et al. |
| 5,788,987 A | 8/1998 | Busetti et al. |
| 6,261,601 B1 | 7/2001 | Talwar et al. |
| 6,284,271 B1 | 9/2001 | Lundberg et al. |
| 6,290,989 B1 | 9/2001 | Asmussen et al. |
| 6,352,721 B1 * | 3/2002 | Faour ............ A61K 9/0004 424/422 |
| 6,365,184 B1 * | 4/2002 | Depui et al. ............ 424/469 |
| 6,776,999 B1 | 8/2004 | Krumme |
| 6,861,072 B1 | 3/2005 | Alaux et al. |
| 2003/0064101 A1 * | 4/2003 | Mehta et al. ............ 424/473 |
| 2004/0180086 A1 * | 9/2004 | Ramtoola et al. ............ 424/466 |

FOREIGN PATENT DOCUMENTS

| | | |
|---|---|---|
| CA | 2 444 601 A1 | 10/2002 |
| JP | 1987-283919 | 12/1987 |
| JP | 2003306428 A | 10/2003 |
| WO | PCT/GB88/00779 * | 9/1988 |
| WO | PCT/GB88/00779 * | 9/1998 |
| WO | WO 99/59637 A1 | 11/1999 |
| WO | WO 00/23045 A1 | 4/2000 |
| WO | 00/66089 A1 | 11/2000 |
| WO | WO 01/10405 A1 | 2/2001 |
| WO | WO 01/10417 A1 | 2/2001 |
| WO | WO 01/10419 A1 | 2/2001 |
| WO | WO 02/00213 A1 | 1/2002 |
| WO | 03/007916 A1 | 1/2003 |
| WO | WO 03/011255 A | 2/2003 |
| WO | 03/097018 A1 | 11/2003 |
| WO | WO 2004/032906 A1 | 4/2004 |

OTHER PUBLICATIONS

Sanjay Garg et al, Gastroretentive Drug Delivery Systems, Business Briefing: Pharmatech 2003, p. No. 160-166.
Gutierrez-Rocca, J. et al., "Progresses in Gastroretentive Drug Delivery Systems", Business Briefing: Pharmaatech 2003, pp. 152-156.

* cited by examiner

Primary Examiner — Suzanne Ziska
(74) Attorney, Agent, or Firm — Sughrue Mion, PLLC

(57) ABSTRACT

The present invention provides a novel gastric retention system in the form of a tablet or a capsule coated with an expandable coating, more particularly, with an expandable coating comprising a film-forming polymer and an expandable component.

12 Claims, No Drawings

GASTRIC RETENTION SYSTEM

FIELD OF THE INVENTION

The present invention relates to a novel gastric retention system in the form of a tablet or a capsule coated with an expandable coating, more particularly, with an expandable coating comprising a film-forming polymer and an expandable component.

BACKGROUND OF THE INVENTION

Gastric retention systems are prepared in different ways. Systems that are capable of swelling and being retained in the gastric environment give a feeling of satiety and can be used in controlling appetite and therefore obesity.

Another subject with a vast amount of work on these systems is the control of drug delivery. The control may be spatial, temporal or both. Controlled drug delivery systems deliver drug to the body so as to establish therapeutically effective blood levels of the active ingredient and once these blood levels are achieved they continue to maintain constant blood levels for long durations by delivering the drug to the body at a slow rate. By avoiding peaks and troughs in blood levels associated with conventional dosage forms, controlled drug delivery systems lower the incidence of adverse effects or side effects. Very importantly controlled drug delivery systems reduce the frequency of dosing leading to convenience to the patient in terms of dosing and compliance to the specified dosage regimens.

It is generally known that the rate at which an oral controlled drug delivery system delivers the drug into the gastrointestinal fluids may not the same as the rate at which it releases the drug into a test aqueous fluid because the gastrointestinal fluid's pH, composition and agitation intensity change with the specific location of the drug delivery system in the gastrointestinal tract i.e. from the stomach to the colon, fasted versus fed state, type and amount of food ingested, and also due to variations in these factors from individual to individual. In addition, the drug may not be absorbed in the same manner and propensity as we move from the stomach to the colon. Some drugs have an "absorption window" i.e. they are absorbed only from the upper parts of the gastrointestinal tract, whereas there are others whose absorption from the colon is not uniform or complete. Thus, the location of the controlled drug delivery system in the gastrointestinal tract as well as the rate at which the controlled drug delivery system moves from the stomach to the colon represent important factors that need to be considered in the design of an oral controlled drug delivery system. It is thus known to those skilled in the art that an oral controlled delivery should be designed not only with a control on the rate at which it releases the drug over the drug delivery time period (temporal control) but also a control on the location from which it is delivered (spatial control). The spatial control can be achieved by prolonging the period of retention of the system in the stomach. Gastric retention systems are also beneficial when the drug is effective locally in the stomach. Drugs absorbed in the upper part of the gastrointestinal tract may exhibit variability in absorption due to inter and intra-individual variability in gastric emptying and gastrointestinal motility. This variation in absorption is addressed partly by a gastric retention drug delivery system and may be further addressed by administering a dosage form comprising the drug such that a part of the drug is available as immediate release, and a part is available as sustained or controlled release.

One of the approaches that has been used for achieving spatial control involves increasing the gastric retention of sustained or controlled drug delivery systems by using a composition containing highly swellable polymers in admixture with a gas-generating agent to form systems that are large in size as well as capable of floating on gastric fluids. It has now become well recognized by those particularly skilled in the art that systems containing swellable polymers will instantly float on gastric fluids because the gas generated and entrapped within the system decreases the density. Swelling to a large size is an important factor in gastric retention of the system. Solids having a size less than 5 to 7 mm show delayed gastric emptying in fed conditions but they can still be emptied from the stomach because their size is smaller than the pyloric sphincter. Even floating systems of size less than 5 to 7 mm can be emptied if the patient is in supine position. The mean resting pyloric diameter is approx. 13+7 mm and it has been reported that dosage forms with a size of approx. 12-18 mm diameter in their expanded state would generally be excluded from the passage of the pyloric sphincter. The system should also be capable of retaining this size in the gastric fluids for long periods under agitational conditions created by gastric motility. Such large intact systems cannot be emptied until the arrival of the interdigestive migrating motor complex at the beginning of the interdigestive phase. The combination of increase in size and floatation results in increased gastric retention of the system. The prior art resulting in this current state of the art is described below.

(A) Swellable Gastric Retention Floating Matrix Drug Delivery Systems

The term "swellable gastric retention floating matrix drug delivery system" herein refers to systems that comprise a drug and an excipient in admixture or in a matrix which is not coated with a polymer coating or not placed inside a polymer envelope or a pouch, and is capable of swelling and floating. Representative prior art illustrating the development of this type of systems is described below.

U.S. Pat. No. 4,777,033 ('033 patent, priority date Jun. 11, 1985) assigned to Teijin Limited, discloses an oral sustained release pharmaceutical preparation comprising a lower alkyl ether of cellulose, polyacrylic acid or its pharmaceutically acceptable salt, a drug, and an effective amount of effervescent foaming agent. Tablets made from the composition however still retained major disadvantages in that the tablets did not remain intact when subjected to dissolution testing. The disintegrated tablet thus does not attain or maintain a size suitable for long duration of retention in the stomach. This prior art presented the problem that if a large amount of gas generating agent, such as sodium bicarbonate, is used in order to sufficiently reduce density and maintain the lowered density for sufficient length of time for achieving floatation of the system, then tablets formed from the same disintegrated.

U.S. Pat. No. 5,651,985 ('985 patent, priority date Feb. 28, 1994) assigned to Bayer AG, claims a pharmacologically active composition comprising a pharmacologically active compound dispersed in a homogenous mixture on the molecular level of polyvinylpyrrolidone and a methacylic acid polymer having an acidic number between 100 and 1,200 mg of KOH/g of polymer solid substance, and optionally a gas-forming additive. With the use of gas-forming additive, the density of the system was reduced on gas generation and the systems were capable of floatation in aqueous medium. The tablets did not disintegrate in an aqueous medium and exhibited marked swelling and high dimensional stability in the swollen state. This dimensional stability was attributed to the non-erodible matrix used in the system. However, the system used relatively low quantities of gas generating agent relative to the '033 patent, and it is not known if the dimensional stability of the system can be maintained when higher quantities of the gas generating additive are used.

U.S. Pat. No. 5,783,212 ('212 patent, priority date Feb. 2, 1996) assigned to Temple University claims a controlled release pharmaceutical tablet comprising a first barrier layer comprising a first swellable, erodible polymer, a drug layer comprising a second swellable, erodible polymer, and a second barrier layer comprising a third swellable, erodible polymer, wherein said first and second barrier layers are adapted to swell and to erode faster than said drug layer; said faster swellability and erodibility of said first and third layers adapted to increase drug delivery from the onset of dissolution. The patent also covers systems wherein at least one of said layers includes a gas-evolving material, which helps the system to float and increases the time of retention of the tablet in the stomach. The patent includes examples wherein the multilayered tablets are obtained by compression and the gas-evolving layer contained relatively larger quantity of the gas-generating agent. All tablets were found to float within about 15 minutes. The examples used polyethylene oxide (PEO) as polymer. Whereas the PEO could retain larger quantity of gas generated by the larger amount of gas generating agent used, the limitation was that the patent exemplified only one polymer that could do so.

U.S. Pat. No. 6,261,601 ('601 patent, priority date Sep. 17, 1997) assigned to Ranbaxy Laboratories used superdisintegrants in the composition. Superdisintegrants are known to swell to several times their volume, their swellability being superior to conventional hydrogel forming swellable polymers such as those used in the '033 patent. The pharmaceutical composition claimed in the patent comprises a drug, a gas-generating component, a swelling agent, a viscolyzing agent, and optionally a gel-forming polymer. The gas generating agents used were carbonates or bicarbonates. The system used viscolyzing agents to prevent disintegration of the system. The drawback of the system was that in order to prevent disintegration of the system, the amounts of superdisintegrant, viscolyzing agent and gas generating agent were required to be optimized. Simultaneously, it was also required that the amounts of excipients be such that the system acquires buoyancy immediately, attains a large expanded size immediately and maintains these characters for sufficient time over which gastric retention is desired. Achieving all these objectives simultaneously is difficult and the formulator may not always be able to do so. Further, the gellable matrix forms an erodible layer on the surface, whereas the core remains dry. Thus, not all of the gas generating agent in the system reacts with the acid of the system. Hence, the buoyancy of the system is capable of being improved by formulating systems where a significant amount of gas generating agent can react with the acid of the environment.

Other prior art references that utilized swellable gastric retention floatation matrix drug delivery systems include WO 0110419A1, WO 0023045A1, WO 0110417A1, WO 03011255A1 and U.S. Pat. No. 6,861,072.

(B) Gas Generating Composition in an Expandable Polymer Envelope or Pouch:

U.S. Pat. No. 3,786,813 ('813 patent, priority date Dec. 27, 1972) assigned to Alza Corporation, claims a drug delivery device for the controlled and continuous administration of a drug to an environment of use comprising a hollow expandable closed member having therein self-contained means for expanding the member, the member being affixed to drug delivery means for delivering a drug at a controlled rate over the given period of time. The patent exemplifies systems wherein a gas generating compartment is connected to a balloon such that the gas generated upon contact with the gastric environment causes the balloon to expand, thereby causing the system to float.

U.S. Pat. No. 4,207,890 ('890 patent, priority date Jan. 4, 1977) assigned to McNeilab, claims a drug dispensing device for controlled and prolonged internal administration of a drug comprising (a) a collapsed, expandable, imperforate envelope made of a substantially non-hydratable, body fluid permeable, drug-permeable polymer film; (b) drug metering means containing said drug and retained by said polymer envelope, whereby drug is dispensed at a predetermined rate; and (c) an effective expandable amount of an expandable agent contained within said polymer envelope, the combination of which agent and which drug when in contact with body fluids cause said polymer envelope to expand to a volume such that the device is retained in the environment of use for at least the minimum desired time. The patent claims systems wherein the polymer film is not applied directly onto the surface of the drug-containing core, but is present in the form of an envelope.

U.S. Pat. No. 4,996,058 ('058 patent, priority date Sep. 18, 1987) assigned to Ciba-Geigy Corporation relates to a dosage form consisting of a sachet which is film coated or filled into capsules, the sachet containing a component that expands on contact with gastric juice and an agent capable of releasing carbon dioxide or nitrogen. The patent does not disclose an expandable coating formed by applying a coating composition comprising a film forming polymer and an expandable component on the surface of a tablet or capsule core, or a method for applying such a coating composition on the surface of a tablet or capsule core. We have found that coating compositions using film forming polymer alone when coated on to tablet or capsule cores of the present invention do not provide desirable floatation, swelling and/or integrity of the system.

U.S. Pat. No. 6,290,989 ('989 patent, priority date Jan. 14, 1997) assigned to LTS Lohmann Therapie-Systeme AG, claims device for the controlled release of active compounds in the gastrointestinal tract with delayed pyloric passage, which device is an improvement over the device of the '890 and '058 patents. The '890 and '058 patents did not provide advice on how the release rate of active compound is to be controlled independently of the permeability of the polymer film forming the sachet. The '989 patent teaches that the active compound can be incorporated in the form of multiparticulates whose nature and composition provides a means for controlling the rate of release of the active compound. Multiparticulates could be present inside the sachet or embedded in the film forming the sachet.

PCT publication number WO 9959637 ('637 patent, priority date May 18, 1998) assigned to LTS Lohmann Therapie-Systeme AG, relates to a device for the controlled release of active agents in the gastrointestinal tract with a prolonged pylorus passage in the form of a bag which expands when the gas generating component of the system generates gas upon contact with gastric juice. The bag is constructed with a polymer membrane made of a monolayered film which controls the release of an active agent located therein, and thus the system has the drawbacks associated with the systems of the '890 and '058 patents, namely, that the release of the active ingredient cannot be controlled independently of the permeability of the polymer film forming the sachet.

U.S. Pat. No. 6,776,999 ('999 patent, priority date Oct. 30, 1998) assigned to LTS Lohmann Therapie-Systeme AG, claims a swallowable, gastroretentive device, which delays passage of the device through the pylorus of the stomach of an orally ingestible pharmaceutical form and releases at least one pharmaceutically active compound in a controlled manner, said device comprising: (a) a pharmaceutical form which contains at least one pharmaceutically active compound; (b) an expandable component which generates gas on contact with gastric juice; and (c) a polymeric membrane system which totally encompasses components (a) and (b) above and is expandable by the gas generated by (b) upon contact with the gastric juice, whereby the polymeric membrane system comprises at least one member selected from the group consisting of a microporous membrane, a porous membrane and a combination of any of the foregoing with a non-porous polymer film. The patent teaches a device in the form of a sachet, which for the purposes of facilitating administration and handling, can be filled into a container made of physiologically acceptable material, for example into hard gelatin capsules.

PCT publication number WO 04032906A1 ('906 patent, priority date Oct. 11, 2002) assigned to DepoMed Development Limited, claims a gastro-retentive dosage form of levodopa for oral administration to a patient in need thereof, said dosage form comprising (a) a tablet comprising a therapeutically effective amount of levodopa, a binder, and a pharmaceutically-acceptable gas-generating agent capable of releasing carbon dioxide upon contact with gastric juice, and (b) an expandable, hydrophilic, water-permeable and substantially gas-impermeable, membrane surrounding the tablet, wherein the membrane expands as a result of the release of carbon dioxide from the gas-generating agent upon contact with the gastric juice, whereby the dosage form becomes too large to pass into the patient's pyloric sphincter. Although the application claims systems wherein the drug-containing core tablet is covered by an expandable, gas-impermeable membrane, the description and examples include systems wherein the drug-containing tablet is introduced into a sachet or pouch made of an expandable, gas-impermeable polyvinyl alcohol membrane. The patent application does not disclose an expandable coating formed by applying a coating composition comprising a film forming polymer and an expandable component on the surface of a tablet or capsule core, or a method for coating such a composition on the surface of a tablet or capsule core.

(C) Gas Generating Composition Coated with Polymer Film:

U.S. Pat. No. 4,101,650 ('650 patent, priority date Apr. 6, 1977) assigned to Zaidan Hojin Biseibutsu Kagalu Kenlcyu Kai discloses a formulation in which granules containing sodium bicarbonate, lactose and polyvinylpyrrolidone are coated with a layer of hydroxypropyl methylcellulose. These are then further coated with a suspension containing the active ingredient pepstatin and hydroxypropyl methylcellulose to form floating minicapsules of a diameter in the range of 0.1 to 2 mm. The drawback of this system is that the minicapsules are much smaller in size than required for long durations of retention in the stomach. Further, the hydroxypropyl methylcellulose layer on the granules is not an expandable polymer film but a film that gels on contact with an aqueous medium.

U.S. Pat. No. 4,844,905 ('905 patent, priority date Feb. 24, 1986) assigned to Eisai Co. discloses granules comprising a drug containing core; a middle gas-generating layer comprising sodium carbonate and organic acid; and an outer coat of an expandable polymer film. Although intended for remaining in the stomach, the granules have the disadvantage of small size. Whereas the coating on the granules works to provide floating granules, we found that when these coatings were used on a tablet or capsule core, the system did not float and the coating disintegrated.

U.S. Pat. No. 6,284,271 ('271 patent, priority date Jul. 1, 1997) assigned to Astrazeneca AB, claims an effervescent dosage form comprising, as a first component, effervescent excipients and as a separate second component, a plurality of individual units comprising a pharmaceutically active compound and optionally pharmaceutically acceptable excipients wherein each unit is provided with a floating generating system comprising at least two coating layers, one of which is a gas generating layer and the other layer is a barrier layer enclosing the generated gas, and wherein the first component is separated from the second component by the layers of the floating generating system. The patent exemplifies dosage forms wherein pellets comprising a core comprising the active ingredient were coated with an inner gas generating layer and an outer hydrophobic polymer layer, followed by mixing of the coated pellets with effervescent excipients and compression into a tablet dosage form. The patent does not disclose an expandable coating formed by coating a composition comprising a film forming polymer and an expandable component on the surface of a tablet or capsule core, or a method for coating such a composition on the surface of a tablet or capsule core.

None of the prior arts described above disclose or teach a gastric retention drug delivery system wherein a tablet or a capsule core is coated with an expandable coating, or teach a method of preparing such a system using suitable coating compositions. We have surprisingly found systems wherein a tablet or capsule core comprising an agent capable of generating internal pressure are coated with a coating composition comprising a film-forming polymer and one or more expandable components.

OBJECTS OF THE INVENTION

It is an object of the present invention to provide a gastric retention drug delivery system in the form of a coated tablet or capsule coated with an expandable coating, such that most or all of the following desirable objectives are achieved simultaneously:

the coating allows rapid permeation of water into the core to activate the agent capable of generating internal pressure on the coat the core and coat are both capable of expansion either the core or the coat or both may be formulated so as to control the rate of release of the therapeutically active agent the system rapidly achieves both buoyancy and a high degree of swelling the coating maintains its physical integrity in contrast to known film-forming compositions which may burst or rupture upon generation of internal pressure the coating maintains the original shape of the device upon expansion the system may be designed to provide the therapeutically active agent in immediate release form and in modified release form.

It is also an object of the present invention to provide a gastric retention system capable of expanding and floating instantaneously in the gastric environment to give a feeling of satiety for use in control of obesity.

SUMMARY OF THE INVENTION

The present invention relates to a gastric retention system in the form of a coated tablet or capsule, wherein the coating comprises one or more film-forming polymers and one or more expandable components, the system being capable of achieving floatation rapidly and capable of expanding to a size suitable for retention of the system in the stomach.

DETAILED DESCRIPTION OF THE INVENTION

The present invention provides a gastric retention system in the form of a coated tablet comprising:
(a) a core in the form of a tablet comprising an agent capable of generating internal pressure on the coat, and
(b) an expandable coating formed by applying a coating composition comprising a film-forming polymer and one or more expandable components on the tablet core.

The system is capable of achieving floatation rapidly and is expandable to a size suitable for retention of the system in the stomach.

The present invention also provides a gastric retention system in the form of a coated capsule, comprising:
(a) a core in the form of a capsule, the core comprising an agent capable of generating internal pressure on the coating, and
(b) an expandable coating formed by applying a coating composition comprising a film-forming polymer and one or more expandable components on the capsule core.

The system is capable of achieving simultaneously the dual desirable properties of instantaneous floatation and expandability to a size suitable for retention of the system in the stomach.

The gastric retention system of the present invention may or may not include a therapeutically active agent. Gastric retention systems of the present invention that do not include the therapeutically active ingredient are capable of swelling and floating in the gastric environment. Due to its expansion in the stomach, it gives a feeling of satiety, thereby reducing the appetite and thus is useful in control of obesity.

The present invention also provides a gastric retention drug delivery system comprising a therapeutically active agent, which system is useful in providing improved delivery of the therapeutically active agent contained therein. The therapeutically active agent may be present in the core, in the coating or both. The therapeutically active agents that may be used in the gastric retention drug delivery system of the present invention may be selected from the following, viz. alcohol abuse preparations, drugs used for alzheimer's disease, anaesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquillizers, drugs used for skin ailments, steroids and hormones.

The core of the gastric retention system of the present invention includes an agent capable of generating internal pressure. The agent generating internal pressure may be selected from gas generating agents, one or more highly swellable polymers, superdisintegrants and mixtures thereof. The gas generating agent used in the core of the gastric retention drug delivery system of the present invention may include a single component that generates gas upon contact with the gastric fluid, or may include a gas generating couple. Gas generating components that may be used in the present invention include solids that liberate gas, especially carbon dioxide or nitrogen, for example under the action of body fluid or the hydrogen ions present therein. Examples include carbonates such as calcium carbonate, bicarbonates such as sodium or potassium bicarbonate, sulfites such as sodium sulfite, sodium bisulfite, or sodium metabisulfite, and the like, ammonium cations or sodium azide or mixtures thereof. These salts may be used alone or in combination with an acid source as a gas generating couple. The acid source may be an edible organic acid, a salt of an edible organic acid, or mixtures thereof. Examples of organic acids that may be used include citric acid, malic acid, succinic acid, tartaric acid, fumaric acid, maleic acid, ascorbic acid, glutamic acid, alginic acid, acrylic acid and their salts, and mixtures thereof. Sodium bicarbonate is used as the preferred gas generating agent. The organic acid may also be a polymer, for example acrylic acid polymers and copolymers such as acrylate polymers available under the tradenames Carbopol®, Eudragit® L-100-55, Eudragit® S-100, Noveon® AA1, which react with carbonates or bicarbonates of alkali or alkali earth metal compounds to generate gas. These are generally used as auxiliary acid sources and may also have properties of themselves generating internal pressure by swelling when in contact with an aqueous medium. The gas-generating agent is used in an amount ranging from about 0.5% to about 50% by weight of the core.

Examples of highly swellable polymers that may be used in the present invention as agents capable of generating internal pressure include, but are not limited to, high molecular weight polyethylene oxide, acrylic acid polymers and copolymers having high swellability, acrylic acid copolymer with vinyl glycol, such as those available under the tradename Noveon® and the like, and mixtures thereof. The highly swellable polymers may be used in an amount ranging from about 0.5% to about 90% by weight of the core. Examples of superdisintegrants that can be used as the agent capable of generating internal pressure include, but are not limited to, crosslinked sodium carboxymethyl cellulose, crosslinked polyvinylpyrrolidone, sodium starch glycolate, ion exchange resins and mixtures thereof. The superdisintegrants may be used in an amount ranging from about 0.5% to about 90% by weight of the core.

The core of the gastric retention system of the present invention may be a compressed tablet obtained by compressing an agent capable of generating internal pressure with pharmaceutically acceptable excipients, and optionally further including a therapeutically active agent, or the core may be a capsule comprising a blend of the agent capable of generating internal pressure with pharmaceutically acceptable excipients, and optionally further including a therapeutically active agent. The core may be homogenous or heterogeneous, i.e. (i) it may be a mixture of the active agent with the agent capable of generating internal pressure, wherein the mixture may be compressed, or (ii) it may be a layered core, wherein the active agent and the agent capable of generating internal pressure are present in two separate layers, further wherein the layers may be laminar or concentric. A capsule or a tablet core may be obtained using conventional methods known to a person skilled in the art.

Various punches and dies may be used to obtain the core, such as for example capsule-shaped, standard concave, oval, triangular and other shapes conventionally used in the pharmaceutical art.

The core of the gastric retention system is coated with a coating composition comprising a film-forming polymer and one or more expandable components. Film-forming polymers used conventionally and known to a person skilled in the art are suitable for use in the coating composition of the present invention. Examples of film-forming polymers that may be used in the present invention include, but are not limited to, cellulose derivatives, acrylic acid polymers and copolymers, polymers of acrylic acid crosslinked with vinyl glycols and mixtures thereof. The film-forming polymer may be used in an amount ranging from about 0.5% to about 70% by weight of the coating composition.

The present invention also provides a gastric retention system wherein the expandable coating comprises (a) a first coating formed by applying a coating composition comprising an agent capable of generating internal pressure on the coat, and (b) a second expandable coating formed by applying a coating composition comprising a film-forming polymer and one or more expandable components on the first coating. Agents that can be used to generate internal pressure, as used in the first coating, are already defined above. The present invention thus provides two types of gastric retention systems—(1) a gastric retention system comprising a tablet or capsule core and an expandable coating comprising a film-forming polymer and one or more expandable components, and (2) a gastric retention system comprising a tablet or capsule core, a first coating comprising an agent capable of generating internal pressure and a second coating comprising a film-forming polymer and one or more expandable components. It may be noted that the expandable coating in the first system is similar to the second coating in the second system, and may be referred to as an outer coat. The first coating of the second system may be referred to as a subcoat. The systems are capable of rapid floatation and expandability to a size suitable for retention of the system in the stomach.

Expandable components that may be used in the outer coat composition are selected from the group comprising gas generating agents, highly swellable polymers, superdisintegrants and mixtures thereof. Gas generating agents that may be used and the amounts in which they may be used are defined herein above. Examples of the highly swellable polymers that may be used in the present invention include:

highly swellable grades of cellulose ethers such as hydroxy $C_{1-4}$ alkyl $C_{1-4}$ alkyl celluloses, carboxyalkyl celluloses, hydroxy $C_{1-4}$ alkyl celluloses preferably hydroxyethylcellulose, hydroxypropylcellulose, hydroxypropyl methylcellulose, more preferably a high viscosity grade of hydroxyethylcellulose;

gums of plant, animal, mineral or synthetic origin such as (i) agar, alginates, carrageenan, furcellaran derived from marine plants, (ii) guar gum, gum arabic, gum tragacanth, karaya gum, locust bean gum, pectin derived from terrestrial plants, (iii) microbial polysaccharides such as dextran, gellan gum, rhamsan gum, welan gum, xanthan gum, and (iv) synthetic or semi-synthetic gums such as propylene glycol alginate, hydroxypropyl guar and modified starches like sodium starch glycolate;

acrylic acid polymers and copolymers, such as cross-linked polymer of acrylic acid with vinyl glycol and commonly known as polycarbophils, polymers available under the tradename Carbopol®, and the like;

a vinyl pyrrolidone polymer such as crosslinked polyvinylpyrrolidone or crospovidone; copolymers of vinyl pyrrolidone and vinyl acetate; or mixtures thereof.

The highly swellable polymers may be used in an amount ranging from about 0.5% to about 40% by weight of the coating composition. Examples of superdisintegrants that may be used include, but are not limited to, cross-linked polyvinylpyrrolidone, cross-linked sodium carboxymethylcellulose, carboxymethyl starch, sodium carboxymethyl starch, potassium methacrylate-divinylbenzene copolymer, polyvinyl alcohols, amylose, cross-linked amylose, starch derivatives, microcrystalline cellulose and cellulose derivatives, alpha-, beta- and gamma-cyclodextrin and dextrin derivatives. The superdisintegrant may be used in an amount ranging from about 0.5% to about 40% by weight of the coating composition. The core is coated to a weight gain of up to about two times the weight of the core with the coating composition. In one embodiment of the present invention, the coating is obtained by using a mixture comprising sodium starch glycolate, sodium bicarbonate, at least one acrylic acid polymer and polycarbophil.

The outer coat composition may further comprise pharmaceutically acceptable excipients such as channel formers selected from water soluble excipients such as mannitol, lactose, halogen salts of alkali and alkaline earth metals, and the like and mixtures thereof. These channel formers may be used in an amount ranging from about 0.5% to about 95% by weight of the coating composition. The coating composition may further comprise pH modifiers such as carbonate and bicarbonate salts of alkali and alkaline earth metal salts, aminosugars such as meglumine, pharmaceutically acceptable acids, and mixtures thereof. These pH modifiers may be used in an amount ranging from about 0.5% to about 50% by weight of the coating composition. The coating composition may comprise anti-tack agents such as talc, colloidal silica and the like. The anti-tack agents may be used in an amount ranging from about 0.5% to about 10% by weight of the coating composition. The coating composition may further comprise plasticisers such as Tweens, diethyl phthalate, polyethylene glycols, and the like, and mixtures thereof. These plasticisers may be used in an amount ranging from about 5% to about 20% by weight of the coating composition. The coating composition may also comprise binders conventionally used in the art. The binders may be used in an amount ranging from about 0.5% to about 50% by weight of the coating composition.

The first coating, or the subcoat as it may be referred to herein, comprises an agent capable of generating internal pressure on the coat. Examples of pharmaceutical excipients that may be used as the agent capable of generating internal pressure, and the amounts in which these may be used are defined herein above. The first coating composition may further comprise a superdisintegrant selected from the group comprising crosslinked sodium carboxymethyl cellulose, crosslinked polyvinylpyrrolidone, sodium starch glycolate, ion exchange resins and mixtures thereof. The superdisintegrant may be used in an amount ranging from about 0.5% to about 90% by weight of the coating composition. The subcoat is coated to a weight gain of about 15% to about 50% by weight of the core. In one embodiment, a mixture of alginic acid, sodium bicarbonate and sodium starch glycolate is used to obtain the subcoat. The first coating may be provided on the core by compression coating, film-coating or dry powder coating technology known to a person skilled in the art.

The outer coat is obtained by coating the tablet or capsule core with a coating composition, which is obtained by mixing the film-forming polymer and the one or more expandable components, such that the expandable component(s) is suspended in a non-solvent vehicle. Alternatively, the core may be coated with a solution or suspension of the film-forming polymer and a dry powder coating of the one or more expandable components using known powder coating technology.

The present invention also provides a novel coating method. The subcoat is deposited on the tablet or capsule core by using a suspension comprising an agent capable of generating internal pressure, such as for example a gas generating couple, in a non-solvent vehicle. The use of a non-solvent vehicle ensures that the gas-generating agent does not start reacting or generating gas while the core is being coated, and until the system contacts an aqueous medium. The outer coat is deposited by using a suspension of the film-forming polymer and one or more expandable components in a non-solvent. The film thus formed is capable of expanding, has exceptional physical strength and is at the same time formed relatively easily. The novel coating method used in the instant invention makes it possible to deposit higher amounts of solids onto the core, which would not have been possible by the conventional film-coating methods known in the art. The novel coating method also makes it possible to use film-forming polymers having a high molecular weight and polymers having high viscosity. Conventional coating methods male it convenient to use only low molecular weight polymers having moderate to low viscosity. Use of high molecular weight and/or high viscosity polymers have not been known in the art to provide continuous films that are capable of expanding and maintaining their physical integrity for prolonged periods of time under conditions of use. The novel coating method of the present invention is also useful in coating gelatin capsules that have been known in the art to be difficult or impossible to coat. Thus, the present invention provides a novel coating composition and a novel method of coating tablets as well as capsules, which method is capable of depositing a higher amount of solids as compared to conventional coating methods, and yet provide a coated dosage form that is compact. It may be noted that although depositing a higher amount of solids on a core is possible by using methods such as compression coating, the coated dosage form thus obtained is relatively large and may be difficult to swallow.

The system of the present invention may also include various pharmaceutically acceptable excipients, for example disintegrants such as starch, cellulose derivatives, gums, crosslinked polymers and the like; binders such as starch, gelatin, sugars, cellulose derivatives, polyvinyl pyrrolidone and the like; lubricants such as talc, magnesium stearate, calcium stearate, aluminum stearate, stearic acid, hydrogenated vegetable oils, colloidal silicon dioxide, polyethylene glycol, cellulose derivatives such as carboxyalkyl cellulose and its alkali salts, and the like; and mixtures thereof.

The system of the present invention may further include a top coat surrounding the outer coat, wherein the top coat is obtained by applying a coating composition comprising a film-forming polymer and a therapeutically active agent that is release immediately. The therapeutically active agent in the top coat may be the same as or different from the therapeutically active agent that may be present in the core of the system. The top coat utilizes film-forming polymers known to a person of skill in the art and used conventionally in the pharmaceutical coating art. Additionally, the system may comprise an inert seal coat between the outer coat and the top coat. The seal coat is obtained by applying a coating composition comprising conventional film-forming agents. The seal coat may also be present between the core and the subcoat or outer coat.

The system of the present invention rapidly swells while maintaining its physical integrity in gastrointestinal fluids and does not rupture or burst. A low density is achieved by entrapment of the gas generated by the gas generating agent such that the system floats in gastric fluids. The swelling and gas entrapment can occur rapidly such that the system, wherein the core is a tablet, is capable of achieving floatation in less than 30 minutes, preferably in less than 15 minutes, when placed in an aqueous medium. The gastric retention system wherein the core is a capsule is capable of floating instantaneously, when placed in an aqueous medium. The gastric retention system of the present invention is capable of swelling to at least twice its original volume in about 30 minutes, when placed in an aqueous medium. The outer coating is expandable in nature and retains its rigidity on expansion, thereby retaining the original shape of the device, even though the core may disintegrate. The swelling, floatation and physical integrity of the outer coat of the system together ensure and increase the time of retention of the system in the gastric milieu.

The therapeutically active agent present in the gastric retention drug delivery system of the present invention may be available in immediate release form or in modified release form, or a combination of immediate release form and modified release form. The system may comprise one or more therapeutically active agents in case of systems that provide controlled release of the therapeutically active agent(s), a pharmaceutically acceptable release rate controlling excipient is present in admixture with the therapeutically active agent(s). The term "in admixture with" as used herein includes a physical mixture of the rate controlling excipient with the active agent in the core, as well as a rate controlling membrane covering a therapeutically active agent composition. For example, the therapeutically active agent may be in the form of controlled release multiparticulates, i.e. in the form of granules, pellets, beads or minipills comprising the therapeutically active agent in admixture with one or more release rate controlling excipients. The multiparticulates may be present in the core or in the coating of the gastric retention drug delivery system of the present invention. The multiparticulates are useful in providing independent control for release of the therapeutically active agent, and also provide isolation of the therapeutically active agent from incompatible excipients. The rate controlling excipients used in the present invention are those that are known to a person skilled in the art and conventionally used.

The present invention may be summarized as follows

A1. A gastric retention system in the form of a coated tablet comprising:
  (a) a core in the form of a tablet comprising an agent capable of generating internal pressure on the coat, and
  (b) an expandable coating formed by applying a coating composition comprising a film-forming polymer and one or more expandable components on the tablet core.

B1. A gastric retention system as described in A1, wherein the agent capable of generating internal pressure is selected from a group comprising gas generating agents, highly swellable polymers, superdisintegrants and mixtures thereof.

C1. A gastric retention drug delivery system comprising a gastric retention system as described in B1 and one or more therapeutically active agents.

D1. A gastric retention drug delivery system as described in C1, wherein the therapeutically active agent is present in the core or the coating or both.

E1. A gastric retention drug delivery system as described in D1, wherein the therapeutically active agents present in the core and the coating are same or different.

F1. A gastric retention system as described in B1, wherein the agent capable of generating internal pressure is a gas generating agent selected from a group comprising carbonates, bicarbonates, sulfites, ammonium cations, sodium azide and mixtures thereof.

G1. A gastric retention system as described in F1, wherein the gas generating agent is present in an amount ranging from about 0.5% to about 50% by weight of the core.

H1. A gastric retention system as described in F1, wherein the agent capable of generating internal pressure is sodium bicarbonate.

I1. A gastric retention system as described in F1, wherein the agent capable of generating internal pressure further comprises an acid source selected from a group comprising organic acids such as citric acid, malic acid, succinic acid, tartaric acid, fumaric acid, maleic acid, ascorbic acid, glutamic acid, alginic acid, acrylic acid or their salts, acrylic acid polymers and copolymers and mixtures thereof.

J1. A gastric retention system as described in B1, wherein the agent capable of generating internal pressure is a superdisintegrant selected from a group comprising crosslinked sodium carboxymethyl cellulose, crosslinked polyvinylpyrrolidone, sodium starch glycolate, ion exchange resins and mixtures thereof.

K1. A gastric retention system as described in J1, wherein the superdisintegrant is present in an amount ranging from about 0.5% to about 90% by weight of the core.

L1. A gastric retention system as described in B1, wherein the agent capable of generating internal pressure is a highly swellable polymer selected from a group comprising high molecular weight polyethylene oxide, acrylic acid polymers and copolymers having high swellability, acrylic acid copolymer with vinyl glycol, and the like and mixtures thereof.

M1. A gastric retention system as described in L1, wherein the highly swellable polymer is present in an amount ranging from about 0.5% to about 90% by weight of the core.

N1. A gastric retention system as described in A1, wherein the coating comprises film-forming polymer selected from the group comprising cellulose derivatives, acrylic acid polymers and copolymers, polymers of acrylic acid crosslinked with vinyl glycols and mixtures thereof.

O1. A gastric retention system as described in N1, wherein the film-forming polymer is used in an amount ranging from about 0.5% to about 70% by weight of the coating composition.

P1. A gastric retention system as described in A1, wherein the expandable component is selected from an agent capable of generating gas, a highly swellable polymer, a superdisintegrant and mixtures thereof.

Q1. A gastric retention system as described in P1, wherein the agent capable of generating gas is selected from a group comprising carbonates, bicarbonates, sulfites, ammonium cations, sodium azide and mixtures thereof.

R1. A gastric retention system as described in Q1, wherein the agent capable of generating gas further comprises an acid source selected from a group comprising organic acids such as citric acid, malic acid, succinic acid, tartaric acid, fumaric acid, maleic acid, ascorbic acid, glutamic acid, alginic acid, acrylic acid or their salts, and mixtures thereof.

S1. A gastric retention system as described in Q1, wherein the agent capable of generating gas is present in an amount ranging from about 0.5% to about 30% by weight of the coating composition.

T1. A gastric retention system as described in Q1, wherein the agent capable of generating gas is sodium bicarbonate.

U1. A gastric retention system as described in T1, wherein the coating further comprises alginic acid.

V1. A gastric retention system as described in P1, wherein the highly swellable polymer is selected from a group comprising cellulose derivatives, acrylic acid polymers and copolymers, polymers of acrylic acid crosslinked with vinyl glycols and mixtures thereof.

W1. A gastric retention system as described in V1, wherein the highly swellable polymer is present in an amount ranging from about 0.5% to about 40% by weight of the coating composition.

X1. A gastric retention system as described in P1, wherein the superdisintegrant is selected from a group comprising crosslinked sodium carboxymethyl cellulose, crosslinked polyvinylpyrrolidone, sodium starch glycolate, ion exchange resins and mixtures thereof.

Y1. A gastric retention system as described in X1, wherein the superdisintegrant is present in an amount ranging from about 0.5% to about 40% by weight of the coating composition.

Z1. A gastric retention system as described in P1, wherein the expandable component is a mixture comprising at least one acrylic acid polymer, sodium starch glycolate, sodium bicarbonate, and polycarbophil.

A2. A gastric retention system as described in A1, wherein the coating composition is coated to a weight gain of up to two times the weight of the core.

B2. A gastric retention drug delivery system as described in C1, wherein one or more therapeutically active agents is present in an immediate release form and/or in a modified release form to provide an immediately releasing dose of one or more of the therapeutically active agents, and/or a modified release dose of the same or different therapeutically active agent(s).

C2. A gastric retention system as described in A1, wherein the system has a floatation time of less than 30 minutes, when placed in an aqueous medium.

D2. A gastric retention system as described in C2, wherein the system has a floatation time of less than 15 minutes, when placed in an aqueous medium.

E2. A gastric retention system as described in A1, wherein the system is capable of swelling to at least about twice its original volume in about 30 minutes, when placed in an aqueous medium.

F2. A gastric retention system in the form of a coated tablet as described in A1, wherein the expandable coating comprises:
(a) a first coating formed by applying a coating composition on the tablet core comprising an agent capable of generating internal pressure on the coat, and
(b) a second coating formed by applying a coating composition comprising a film-forming polymer and one or more expandable components on the first coating.

G2. A gastric retention system as described in F2, wherein the agent capable of generating internal pressure in the first coating is selected from a group comprising gas generating agents, highly swellable polymers, superdisintegrants and mixtures thereof.

H2. A gastric retention drug delivery system comprising a gastric retention system as described in G2 and one or more therapeutically active agents.

I2. A gastric retention system as described in G2, wherein the first coating composition further comprises a superdisintegrant selected from a group comprising crosslinked sodium carboxymethyl cellulose, crosslinked polyvinylpyrrolidone, sodium starch glycolate, ion exchange resins and mixtures thereof.

J2. A gastric retention system as described in G2, wherein the first coating composition is coated to a weight gain of about 15% to about 50% by weight of the core.

K2. A gastric retention system as described in G2, wherein the second coating composition is coated to a weight gain of up to two times the weight of the core coated with the first coating.

L2. A gastric retention drug delivery system as described in C1, wherein the system further comprises a top coating comprising a film-forming polymer and a therapeutically active agent that is released immediately.

M2. A gastric retention drug delivery system as described in H2, wherein the system further comprises a top coating comprising a film-forming polymer and a therapeutically active agent that is released immediately N2. A gastric retention drug delivery system as described in C1, wherein the system further comprises a therapeutically active agent in the form of particles embedded in the coating.

O2. A gastric retention drug delivery system as described in C1, wherein the system further comprises controlled release multiparticulates comprising one or more therapeutically active agents.

P2. A gastric retention drug delivery system as described in O2, wherein the multiparticulates may be present in the core, in the coating or both.

Q2. A gastric retention system as described in A1, wherein the expandable coating is such that it maintains the original shape of the system upon expansion.

R2. A gastric retention system in the form of a coated capsule, comprising:
  (a) a core in the form of a capsule, the core comprising an agent capable of generating internal pressure on the coating, and
  (b) an expandable coating formed by applying a coating composition comprising a film-forming polymer and one or more expandable components on the capsule core.

S2. A gastric retention system as described in R2, wherein the agent capable of generating internal pressure is selected from a group comprising gas generating agents, highly swellable polymers, superdisintegrants and mixtures thereof.

T2. A gastric retention drug delivery system comprising a gastric retention system as described in S2 and one or more therapeutically active agents.

U2. A gastric retention drug delivery system as described in T2, wherein the therapeutically active agent is present in the core and the coating.

U2. A gastric retention drug delivery system as described in T2, wherein the therapeutically active agents present in the core and the coating are same or different.

V2. A gastric retention system as described in S2, wherein the agent capable of generating internal pressure is a gas generating agent selected from a group comprising carbonates, bicarbonates, sulfites, ammonium cations, sodium azide and mixtures thereof.

W2. A gastric retention system as described in V2, wherein the gas generating agent is present in an amount ranging from about 0.5% to about 50% by weight of the core.

X2. A gastric retention system as described in W2, wherein the agent capable of generating internal pressure is sodium bicarbonate.

Y2. A gastric retention system as described in X2, wherein the agent capable of generating internal pressure further comprises an acid source selected from a group comprising organic acids such as citric acid, malic acid, succinic acid, tartaric acid, fumaric acid, maleic acid, ascorbic acid, glutamic acid, alginic acid, acrylic acid or their salts, acrylic acid polymers and copolymers and mixtures thereof.

Z2. A gastric retention system as described in S2, wherein the agent capable of generating internal pressure is a highly swellable polymer selected from a group comprising crosslinked sodium carboxymethyl cellulose, crosslinked polyvinylpyrrolidone, sodium starch glycolate, ion exchange resins and mixtures thereof.

A3. A gastric retention system as described in Z2, wherein the highly swellable polymer is present in an amount ranging from about 0.5% to about 90% by weight of the core.

B3. A gastric retention system as described in R2, wherein the coating comprises film-forming polymer selected from the group comprising cellulose derivatives, acrylic acid polymers and copolymers, polymers of acrylic acid crosslinked with vinyl glycols and mixtures thereof.

C3. A gastric retention system as described in B3, wherein the film-forming polymer is used in an amount ranging from about 0.5% to about 70% by weight of the coating composition.

D3. A gastric retention system as described in R2, wherein the coating comprises an expandable component selected from an agent capable of generating gas, a highly swellable polymer, a superdisintegrant and mixtures thereof.

E3. A gastric retention system as described in D3, wherein the agent capable of generating gas is selected from a group comprising carbonates, bicarbonates, sulfites, ammonium cations, sodium azide and mixtures thereof.

F3. A gastric retention system as described in E3, wherein the agent capable of generating internal pressure further comprises an acid source selected from a group comprising organic acids such as citric acid, malic acid, succinic acid, tartaric acid, fumaric acid, maleic acid, ascorbic acid, glutamic acid, alginic acid, acrylic acid or their salts, and mixtures thereof.

G3. A gastric retention system as described in E3, wherein the agent capable of generating gas is present in an amount ranging from about 0.5% to about 30% by weight of the coating composition.

H3. A gastric retention system as described in E3, wherein the agent capable of generating gas is sodium bicarbonate.

I3. A gastric retention system as described in D3, wherein the superdisintegrant is selected from a group comprising crosslinked sodium carboxymethyl cellulose, crosslinked polyvinylpyrrolidone, sodium starch glycolate, ion exchange resins and mixtures thereof.

J3. A gastric retention system as described in I3, wherein the superdisintegrant is present in an amount ranging from about 0.5% to about 40% by weight of the coating composition.

K3. A gastric retention system as described in D3, wherein the highly swellable polymer is selected from a group comprising cellulose derivatives, acrylic acid polymers and copolymers, polymers of acrylic acid crosslinked with vinyl glycols and mixtures thereof.

L3. A gastric retention system as described in K3, wherein the highly swellable polymer is present in an amount ranging from about 0.5% to about 40% by weight of the coating composition.

M3. A gastric retention system as described in D3, wherein the expandable component is a mixture comprising at least one acrylic acid polymer, sodium starch glycolate, sodium bicarbonate, and polycarbophil.

N3. A gastric retention system as described in R2, wherein the coating composition is coated to a weight gain of up to two times the weight of the core.

O3. A gastric retention drug delivery system as described in T2, wherein one or more therapeutically active agents is present in an immediate release form and/or in a modified release form to provide an immediately releasing dose of one or more of the therapeutically active agents, and/or a modified release dose of the same or different therapeutically active agent(s).

P3. A gastric retention system as described in R2, wherein the system is capable of swelling to at least about twice its original volume in about 30 minutes, when placed in an aqueous medium.

Q3. A gastric retention system as described in R2, wherein the system is capable of instantaneously floating, when placed in an aqueous medium.

R3. A gastric retention system in the form of a coated capsule as described in R2, wherein the expandable coating comprises:
(a) a first coating formed by applying a coating composition comprising an agent capable of generating internal pressure on the coat, and
(b) a second expandable coating formed by applying a coating composition comprising a film-forming polymer and one or more expandable components on the first coating.

S3. A gastric retention system as described in R3, wherein the agent capable of generating internal pressure in the first coating composition is selected from an agent capable of generating gas, a highly swellable polymer, a superdisintegrant and mixtures thereof.

T3. A gastric retention drug delivery system comprising a gastric retention system as described in S3 and one or more therapeutically active agents.

U3. A gastric retention drug delivery system as described in T3 where the therapeutically active agent is present in the core, in the coating or both.

V3. A gastric retention system as described in S3, wherein the superdisintegrant is selected from a group comprising crosslinked sodium carboxymethyl cellulose, crosslinked polyvinylpyrrolidone, sodium starch glycolate, ion exchange resins and mixtures thereof.

W3. A gastric retention system as described in R3, wherein the first coating composition is coated to a weight gain of about 15% to about 50% by weight of the core.

X3. A gastric retention system as described in R3, wherein the second coating composition is coated to a weight gain of up to two times the weight of the core coated with the first coating.

Y3. A gastric retention drug delivery system as described in T2, wherein the system further comprises a top coating comprising a film-forming polymer and a therapeutically active agent that is released immediately.

Z3. A gastric retention drug delivery system as described in T3, wherein the system further comprises a top coating comprising a film-forming polymer and a therapeutically active agent that is released immediately.

A4. A gastric retention drug delivery system as described in T2, wherein the system further comprises a therapeutically active agent in the form of particles embedded in the coating.

B4. A gastric retention drug delivery system as described in T2, wherein the system further comprises controlled release multiparticulates comprising one or more therapeutically active agents.

C4. A gastric retention drug delivery system as described in B4, wherein the multiparticulates may be present in the core, in the coating or both.

D4. A gastric retention system as described in R2, wherein the expandable coating is such that it maintains the original shape of the system upon swelling.

E4. A process for coating a tablet or capsule core comprising applying a coating composition comprising expandable components in a dry powder form or suspended in a non-solvent vehicle.

F4. A process as described in E4, wherein the expandable component is selected from an agent capable of generating gas, a highly swellable polymer, a superdisintegrant and mixtures thereof.

G4. A process as described in F4, wherein the agent capable of generating gas is selected from a group comprising carbonates, bicarbonates, sulfites, ammonium cations, sodium azide and mixtures thereof.

H4. A process as described in G4, wherein the agent capable of generating internal pressure further comprises an acid source selected from a group comprising organic acids such as citric acid, malic acid, succinic acid, tartaric acid, fumaric acid, maleic acid, ascorbic acid, glutamic acid, alginic acid, acrylic acid or their salts, and mixtures thereof.

I4. A process as described in G4, wherein the agent capable of generating gas is present in an amount ranging from about 0.5% to about 30% by weight of the coating composition.

J4. A process as described in G4, wherein the agent capable of generating gas is sodium bicarbonate.

K4. A process as described in F4, wherein the superdisintegrant is selected from a group comprising crosslinked sodium carboxymethyl cellulose, crosslinked polyvinylpyrrolidone, sodium starch glycolate, ion exchange resins and mixtures thereof.

L4. A process as described in K4, wherein the superdisintegrant is present in an amount ranging from about 0.5% to about 40% by weight of the coating composition.

M4. A process as described in F4, wherein the highly swellable polymer is selected from a group comprising cellulose derivatives, acrylic acid polymers and copolymers, polymers of acrylic acid crosslinked with vinyl glycols and mixtures thereof.

N4. A process as described in M4, wherein the highly swellable polymer is present in an amount ranging from about 0.5% to about 40% by weight of the coating composition.

O4. A process as described in F4, wherein the expandable component is a mixture comprising at least one acrylic acid polymer, sodium starch glycolate, sodium bicarbonate, and polycarbophil.

The examples that follow do not limit the scope of the invention and are merely used as illustrations.

Comparative Example 1

A gastric retention drug delivery system comprising metformin was obtained as mentioned in Table 1 below.

TABLE 1

| Ingredients | Quantity (mg/tablet) | Quantity (% w/w) |
|---|---|---|
| Core | | |
| Metformin hydrochloride | 1000.0 | 81.97 |
| Hydroxypropyl methylcellulose (HPMC E50 LV) | 20.0 | 1.64 |
| Polyvinylpyrrolidone (PVP K-90F) | 20.0 | 1.64 |
| Crospovidone | 40.0 | 3.28 |
| Sodium bicarbonate | 15.0 | 1.23 |
| Silicified microcrystalline cellulose (Prosolv SMCC 90) | 100.0 | 8.19 |
| Colloidal silicon dioxide | 7.0 | 0.57 |
| Talc | 9.0 | 0.74 |
| Magnesium stearate | 9.0 | 0.74 |
| Subcoat | | |
| Alginic acid | 107.81 | Coated to a weight gain of about 20% by weight of the core |
| Sodium bicarbonate | 21.56 | |
| Sodium starch glycolate | 53.9 | |
| Mannitol SD 25 | 26.95 | |
| Polyvinylpyrrolidone (PVP K-90F) | 25.15 | |
| Talc | 6.47 | |
| Tween 20 | 2.16 | |
| Outer coat | | |
| Eudragit L-100-55 | 105.78 | Coated to a weight gain of about 8.5% by weight of the subcoated core |
| Tween 20 | 0.74 | |
| Polyethylene glycol (PEG 400) | 1.86 | |
| Talc | 2.97 | |

Metformin hydrochloride, HPMC E50LV, crospovidone and PVP K-90F were mixed and granulated using purified water. The granules thus obtained were dried, milled and mixed with sodium bicarbonate, crospovidone, Prosolv SMCC 90, colloidal silicon dioxide, talc and magnesium stearate. The blend thus obtained was compressed to obtain the core. This core was then coated with a suspension comprising alginic acid, sodium bicarbonate, sodium starch glycolate, mannitol, PVP K-90F, talc and Tween 20 in isopropyl alcohol to a weight gain of 20% by weight of the core to obtain the subcoat. This was further coated with a coating composition comprising Eudragit L-100-55, tween 20, PEG 400 and talc in isopropyl alcohol to a weight gain of about 8.5% by weight of the subcoated core.

The tablets thus obtained, when placed in 100 ml of 0.01 N hydrochloric acid, did not float for up to 8 hours. The tablets also did not swell sufficiently, i.e. they were found to swell to only about 1.5 times their volume at the end of 20 hours. Thus, the tablets of this example did not possess desirable characteristics for consistent and prolonged gastric retention.

Comparative Example 2

A gastric retention drug delivery system comprising the core as mentioned in comparative example 1, and which is coated with a subcoat as mentioned in comparative example 1, was coated with an outer coat as mentioned in Table 2 below.

TABLE 2

| Ingredients | Quantity (% w/w) | |
|---|---|---|
| Outer coat | | |
| Hydroxypropyl methylcellulose (HPMC E5) | 13.04 | Coated to a weight gain of about 8.5% by weight of the subcoated core |
| Eudragit L-100-55 | 73.91 | |
| Tween 20 | 0.59 | |
| PEG 400 | 1.49 | |
| Talc | 2.39 | |

The subcoated tablet was prepared as mentioned in comparative example 1 above. The outer coat was obtained by coating with a solution of HPMC E5, Eudragit L-100-55 and the coating aids in isopropyl alcohol and dichloromethane, to a weight gain of 8.5% by weight of the subcoated core.

The tablets thus obtained were evaluated as regards the time required to float, i.e. buoyancy time, and the swelling index, i.e. increase in volume of the dosage form. The results are recorded in Table 3 below.

TABLE 3

| Medium used | Buoyancy time (minutes) | Swelling index at the end of 30 minutes |
|---|---|---|
| 0.01N HCl | Did not float till ~7 hours | 1.1 |
| pH 4.5 buffer | Did not float till ~7 hours | 1.1 |

The tablets did not float till about 7 hours. Small blisters were seen on the coating at the end of 30 minutes, the coating ruptured within 1 hour and gas was observed to escape in the form of bubbles. Such a coating therefore would not be suitable for a gastric retention system.

Example 1

A gastric retention drug delivery system comprising metformin was obtained as mentioned in Table 4 below.

TABLE 4

| Ingredients | Quantity (mg/tablet) | Quantity (% w/w) |
|---|---|---|
| Core | | |
| Metformin hydrochloride | 750.0 | 81.97 |
| Hydroxypropyl methylcellulose (HPMC E50 LV) | 15.0 | 1.64 |
| Polyvinylpyrrolidone (PVP K-90F) | 15.0 | 1.64 |
| Crospovidone | 30.0 | 3.28 |
| Sodium bicarbonate | 11.25 | 1.23 |
| Silicified microcrystalline cellulose (Prosolv SMCC 90) | 75.0 | 8.19 |
| Colloidal silicon dioxide | 5.25 | 0.57 |
| Talc | 6.75 | 0.74 |
| Magnesium stearate | 6.75 | 0.74 |
| Subcoat | | |
| Alginic acid | 76.00 | Coated to a weight gain of about 20% by weight of the core |
| Sodium bicarbonate | 15.30 | |
| Sodium starch glycolate | 38.00 | |
| Mannitol SD 25 | 19.00 | |
| Polyvinylpyrrolidone (PVP K-90F) | 17.70 | |
| Talc | 4.50 | |
| Tween 20 | 1.50 | |
| Outer coat | | |
| Noveon AA1 | 5.64 | Coated to a weight gain of about 8.5% |
| Sodium bicarbonate | 11.30 | |
| Eudragit L-100-55 | 45.12 | |
| Mannitol SD 25 | 45.12 | |

TABLE 4-continued

| Ingredients | Quantity (mg/tablet) | Quantity (% w/w) |
|---|---|---|
| Sodium starch glycolate | 13.16 | |
| Tween 20 | 0.75 | |
| PEG 400 | 1.90 | |
| Talc | 3.01 | |
| Top coat | | |
| Metformin hydrochloride | 250.0 | Coated to a weight gain of about 24% |
| Opadry YS-2-7013 Clear | 35.0 | |

The subcoated core was obtained as mentioned in comparative example 1 above. This was further coated with a coating composition comprising Noveon AA1, sodium bicarbonate, Eudragit L-100-55, mannitol, sodium starch glycolate, Tween 20, PEG 400, talc and isopropyl alcohol to a weight gain of about 8.5% by weight. The tablets thus obtained were coated with a top coat comprising an immediate release fraction of metformin hydrochloride to a weight gain of about 24% using a coating solution comprising metformin hydrochloride and Opadry.

The coating solutions used to obtain the subcoat and the outer coat, in this and all other examples, were prepared by mixing the ingredients of the coating composition and suspending them in a suitable carrier, stirring the mixture with an overhead stirrer, followed by introducing the mixture in a colloid mill. The mixture was milled for about 30 minutes and the dispersion so obtained was used for coating.

The tablets were subjected to dissolution studies using United States Pharmacopoeia dissolution apparatus, type II, at 50 rpm, using 1000 ml of the dissolution medium. The results are recorded in Table 5 below.

TABLE 5

| Time (hours) | Cumulative % dissolved | | |
|---|---|---|---|
| Dissolution medium used | 0.01N HCl | pH 3.0 buffer | pH 4.5 buffer |
| 0 | 0 | 0 | 0 |
| 1 | 19 | 23 | 21 |
| 2 | 23 | 24 | 24 |
| 4 | 36 | 35 | 44 |
| 8 | 63 | 65 | 80 |
| 12 | 82 | 81 | 92 |
| 16 | 89 | 89 | 96 |
| 20 | 93 | 96 | 98 |
| 24 | 96 | 97 | 100 |

The tablets were evaluated as regards the time required to float, i.e. buoyancy time, and the swelling index, i.e. increase in volume of the dosage form. The tablets were introduced in 100 ml of 0.01 N HCl and pH 4.5 buffer to evaluate these. The swelling index of the dosage forms of the present invention was calculated as follows. The dosage form as manufactured, although a capsule or a caplet, was assumed to have the volume equivalent to a three-dimensional, solid, cylinder, i.e. the curved edges of the capsule/caplet were disregarded, and the volume was calculated accordingly. The swelling index was calculated as the increase in volume of the dosage form at the end of 30, 60, 120 and 240 minutes, assuming the swollen mass also to be a cylinder. The results are recorded in Table 6 below, wherein the buoyancy time is in minutes, and the swelling index is the number of times the volume of the dosage form increases as a function of time.

TABLE 6

| Medium used | Buoyancy time (minutes) | Swelling index | | |
|---|---|---|---|---|
| | | 30 min | 60 min | 120 min |
| 0.01N HCl | 33 | ~1.8 | ~2.14 | ~2.5 |
| pH 3.0 buffer | 27 | ~1.8 | ~1.9 | ~2.5 |
| pH 4.5 buffer | 12 | — | ~2.26 | ~3.15 |

It is therefore apparent from the above example that the composition of the outer coat significantly affects the buoyancy and the swelling index of the gastric retention drug delivery system of the present invention.

Example 2

A gastric retention drug delivery system comprising a subcoated core similar to that used in example 1, was coated with an outer coating composition mentioned in Table 7 below.

TABLE 7

| Ingredients | Quantity (% w/w) | |
|---|---|---|
| Outer coat | | |
| Noveon AA1 | 13.46 | Coated to a weight gain of about 8.5% by weight of the subcoated core |
| Eudragit L-100-55 | 45.28 | |
| Mannitol SD 25 | 22.64 | |
| Sodium starch glycolate | 13.46 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 8 below.

TABLE 8

| Medium used | Buoyancy time (minutes) | Swelling index | | |
|---|---|---|---|---|
| | | 30 min | 60 min | 120 min |
| 0.01N HCl | ~10-12 | 2.3 | 2.3 | 2.4 |
| pH 4.5 buffer | ~8-9 | 4 | 5.38 | 9.9 |

Example 3

A gastric retention drug delivery system comprising a subcoated core similar to that used in example 1, was coated with an outer coating composition mentioned in Table 9 below.

TABLE 9

| Ingredients | Quantity (% w/w) | |
|---|---|---|
| Outer coat | | |
| Eudragit L-100-55 | 52.17 | Coated to a weight gain of about 8.5% by weight of the subcoated core |
| Mannitol SD 25 | 26.08 | |
| Sodium starch glycolate | 15.21 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 10 below.

TABLE 10

| Medium used | Buoyancy time (minutes) | Swelling index | | | |
|---|---|---|---|---|---|
| | | 30 min | 60 min | 120 min | 24 hours |
| 0.01N HCl | ~13-14 | 2.6 | 2.4 | 3 | 16.6 |
| pH 4.5 buffer | ~13-14 | 2.5 | 2.5 | 3 | 11.2 |

Example 4

A gastric retention drug delivery system comprising a subcoated core similar to that used in example 1, was coated with an outer coating composition mentioned in Table 11 below.

TABLE 11

| Ingredients | Quantity (% w/w) | |
|---|---|---|
| Outer coat | | |
| Noveon AA1 | 2.29 | Coated to a weight |
| Sodium bicarbonate | 9.16 | gain of about 8.5% |
| Eudragit L-100-55 | 36.64 | by weight of the |
| Mannitol SD 25 | 36.64 | subcoated core |
| Sodium starch glycolate | 10.69 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 12 below.

TABLE 12

| Medium used | Buoyancy time (minutes) | Swelling index | | | |
|---|---|---|---|---|---|
| | | 30 min | 60 min | 120 min | 24 hours |
| 0.01N HCl | ~7 | 2 | 2.8 | 3.5 | 5.5 |
| pH 4.5 buffer | ~7 | 2.7 | 4.1 | 5 | 10.5 |

Example 5

A gastric retention drug delivery system comprising a subcoated core similar to that used in example 1, was coated with an outer coating composition mentioned in Table 13 below.

TABLE 13

| Ingredients | Quantity (% w/w) | |
|---|---|---|
| Outer coat | | |
| Eudragit L-100-55 | 40.68 | Coated to a weight |
| Sodium bicarbonate | 10.17 | gain of about 8.5% |
| Sodium starch glycolate | 16.95 | by weight of the |
| Mannitol SD 25 | 27.12 | subcoated core |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 14 below.

TABLE 14

| Medium used | Buoyancy time (minutes) | Swelling index 24 hours |
|---|---|---|
| 0.01N HCl | ~1 | 8.2 |
| pH 4.5 buffer | ~5-6 | 9.1 |

Example 6

A gastric retention drug delivery system comprising a subcoated core similar to that used in example 1, was coated with an outer coating composition mentioned in Table 15 below.

TABLE 15

| Ingredients | Quantity (% w/w) | |
|---|---|---|
| Outer coat | | |
| Eudragit L-100-55 | 33.89 | Coated to a weight |
| Hydroxypropyl methylcellulose | 11.86 | gain of about 8.5% |
| Sodium bicarbonate | 10.17 | by weight of the |
| Sodium starch glycolate | 11.86 | subcoated core |
| Mannitol SD 25 | 27.12 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 16 below.

TABLE 16

| Medium used | Buoyancy time (minutes) | Swelling index | | |
|---|---|---|---|---|
| | | 30 min | 60 min | 120 min |
| 0.01N HCl | ~6 | 2.6 | 2.7 | 3.6 |
| pH 4.5 buffer | ~6 | 2.8 | 2.9 | 3.6 |

Example 7

A gastric retention drug delivery system comprising a subcoated core similar to that used in example 1, was coated with an outer coating composition mentioned in Table 17 below.

TABLE 17

| Ingredients | Quantity (% w/w) | |
|---|---|---|
| Outer coat | | |
| Eudragit L-100-55 | 32.88 | Coated to a weight |
| Noveon AA1 | 4.11 | gain of about 8.5% |
| Sodium bicarbonate | 8.22 | by weight of the |
| Sodium starch glycolate | 9.59 | subcoated core |
| Mannitol SD 25 | 41.09 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 18 below.

TABLE 18

| Medium used | Buoyancy time (minutes) | Swelling index | | |
|---|---|---|---|---|
| | | 30 min | 60 min | 120 min |
| 0.01N HCl | ~8-12 | 1.7 | 2.8 | 3.5 |
| pH 4.5 buffer | ~8-9 | 1.7 | 4.2 | 5 |

Example 8

A gastric retention drug delivery system comprising a subcoated core similar to that used in example 1, was coated with an outer coating composition mentioned in Table 19 below.

TABLE 19

| Ingredients | Quantity (% w/w) | |
|---|---|---|
| Outer coat | | |
| Eudragit L-100-55 | 40.68 | Coated to a weight gain of about 8.5% by weight of the subcoated core |
| Noveon AA1 | 5.08 | |
| Sodium bicarbonate | 10.17 | |
| Sodium starch glycolate | 11.86 | |
| Mannitol SD 25 | 27.12 | |
| Tween 20 | 0.59 | |
| PEG 400 | 1.49 | |
| Talc | 2.39 | |

The tablets thus obtained were evaluated as regards the time required to float, i.e. buoyancy time, and the swelling index, i.e. increase in volume of the dosage form. The results are recorded in Table 20 below.

TABLE 20

| Medium used | Buoyancy time (minutes) | Swelling index | | |
|---|---|---|---|---|
| | | 30 min | 60 min | 120 min |
| 0.01N HCl | ~8 | 2.8 | 2.5 | 3.3 |
| pH 4.5 buffer | ~8 | 3.5 | 3.5 | 5.9 |

Example 9

A gastric retention drug delivery system comprising baclofen was prepared as mentioned in Table 21 below.

TABLE 21

| Ingredients | Quantity (mg/capsule) | Quantity (% w/w) |
|---|---|---|
| Core | | |
| Baclofen | 22.5 | 5.49 |
| Fumaric acid | 10.0 | 2.44 |
| Mannitol SD 200 | 264.5 | 64.5 |
| Hydroxypropyl cellulose (HXF) | 68.0 | 16.59 |
| Sodium bicarbonate | 30.0 | 7.32 |
| Colloidal silicon dioxide | 5.0 | 1.22 |
| Talc | 5.0 | 1.22 |
| Magnesium stearate | 5.0 | 1.22 |

TABLE 21-continued

| Ingredients | Quantity (mg/capsule) | Quantity (% w/w) |
|---|---|---|
| Subcoat | | |
| Alginic acid | 54.35 | Coated to a weight gain of about 25% by weight of the core |
| Sodium bicarbonate | 10.87 | |
| Sodium starch glycolate | 27.17 | |
| Mannitol SD 25 | 13.59 | |
| Polyvinylpyrrolidone (PVP K-90F) | 16.30 | |
| Talc | 3.26 | |
| Tween 20 | 1.09 | |
| Outer coat | | |
| Noveon AA1 | 4.41 | Coated to a weight gain of about 18% by weight |
| Sodium bicarbonate | 8.82 | |
| Eudragit L-100-55 | 35.29 | |
| Eudragit S-100 | 8.82 | |
| Mannitol SD 25 | 35.29 | |
| Sodium starch glycolate | 10.29 | |
| Tween 20 | 0.59 | |
| Polyethylene glycol (PEG 400) | 1.47 | |
| Talc | 2.35 | |
| Diethyl phthalate | 6.62 | |
| Top Coat | | |
| Baclofen | 7.5 | Coated to a weight gain of about 1.5% |
| Polyvinylpyrrolidone (Povidone K-30) | 1.50 | |
| Talc | 2.25 | |
| Tween 20 | 0.40 | |

Baclofen, fumaric acid, mannitol, hydroxypropyl cellulose, sodium bicarbonate, colloidal silicon dioxide, talc and magnesium stearate were mixed to obtain a blend and this was filled in size 0 hard gelatin capsules. The filled capsules were coated with a coating suspension containing alginic acid, sodium bicarbonate, sodium starch glycolate, mannitol, povidone, talc, Tween 20 in isopropyl alcohol to a weight gain of about 25% by weight of the core capsules. This was followed by introduction of the outer coat using a coating solution comprising Noveon AA1, sodium bicarbonate, Eudragit L-100-55, Eudragit S-100, mannitol, sodium starch glycolate, Tween 20, PEG, talc and diethyl phthalate in isopropyl alcohol, the solution being coated to about 18% by weight. Finally, a top coat comprising baclofen, povidone K-30, talc and Tween 20 was introduced on the capsules to a weight gain of about 1.5%, using a coating solution in purified water.

The capsules thus obtained were found to float immediately upon immersion in an aqueous medium. The capsules were evaluated as regards the swelling index, i.e. increase in volume of the dosage form. The results are recorded in Table 22 below.

TABLE 22

| Medium used | Swelling index | | |
|---|---|---|---|
| | 30 min | 60 min | 120 min |
| 0.01N HCl | ~2.12 | ~2.5 | ~3.0 |
| pH 4.5 buffer | ~2.84 | ~3.15 | ~3.53 |

Example 10

A gastric retention drug delivery system comprising carbidopa and levodopa was prepared as mentioned in Table 23 below.

TABLE 23

| Ingredients | Quantity (mg/capsule) | Quantity (% w/w) |
|---|---|---|
| Core | | |
| Carbidopa monohydrate | 41.3 | 7.5 |
| Levodopa | 150.0 | 27.27 |
| Fumaric acid | 10.0 | 1.82 |
| Mannitol SD 200 | 161.7 | 29.4 |
| Crospovidone | 25.0 | 4.55 |
| Colloidal silicon dioxide | 3.0 | 0.55 |
| Silicified microcrystalline cellulose (Prosolv SMCC 90) | 150.0 | 27.27 |
| Talc | 4.5 | 0.82 |
| Magnesium stearate | 4.5 | 0.82 |
| Subcoat | | |
| Alginic acid | 54.35 | Coated to a weight gain of about 20% by weight of the core |
| Sodium bicarbonate | 10.87 | |
| Sodium starch glycolate | 27.17 | |
| Mannitol SD 25 | 13.59 | |
| Polyvinylpyrrolidone (PVP K-90F) | 16.30 | |
| Talc | 3.26 | |
| Tween 20 | 1.09 | |
| Outer coat | | |
| Noveon AA1 | 4.41 | Coated to a weight gain of about 14.5% by weight of the core coated with the subcoat |
| Sodium bicarbonate | 8.82 | |
| Eudragit L-100-55 | 32.35 | |
| Eudragit S-100 | 2.94 | |
| Mannitol SD 25 | 44.11 | |
| Sodium starch glycolate | 10.29 | |
| Tween 20 | 0.59 | |
| Polyethylene glycol (PEG 400) | 1.47 | |
| Talc | 2.35 | |
| Diethyl phthalate | 5.29 | |
| Seal Coat | | |
| Opadry white YS-1-7003 | Coated to a weight gain of about 3% | |
| Top Coat | | |
| Carbidopa | 12.50 | Coated to a weight gain of about 11% by weight of seal coated core |
| Levodopa | 50.0 | |
| Polyvinylpyrrolidone (PVP K-30) | 12.50 | |
| Talc | 20.83 | |
| Tween 20 | 3.33 | |

The coated capsules were prepared as mentioned in examples above.

Example 11

A gastric retention drug delivery system comprising baclofen was prepared as mentioned in Table 24 below.

TABLE 24

| Ingredients | Quantity (mg/capsule) | Quantity (% w/w) |
|---|---|---|
| Core | | |
| Baclofen | 22.5 | 5.49 |
| Fumaric acid | 10.0 | 2.44 |
| Mannitol SD 200 | 200.5 | 48.90 |
| Noveon AA1 | 108.0 | 26.34 |
| Sodium bicarbonate | 54.0 | 13.17 |
| Colloidal silicon dioxide | 5.0 | 1.22 |
| Talc | 5.0 | 1.22 |
| Magnesium stearate | 5.0 | 1.22 |

The core was obtained by blending the excipients with baclofen and filling it in a hard gelatin capsule. The capsule was then coated with a subcoat and outer coat similar to examples above.

Example 12

A gastric retention drug delivery system comprising baclofen was obtained as mentioned in Table 25 below.

TABLE 25

| Ingredients | Quantity (mg/tablet) | Quantity (% w/w) |
|---|---|---|
| Core | | |
| Baclofen | 22.5 | 3.38 |
| Fumaric acid | 10.0 | 1.50 |
| Mannitol SD 200 | 264.50 | 39.77 |
| Crospovidone | 55.0 | 8.27 |
| Sodium bicarbonate | 30.0 | 4.51 |
| Silicified microcrystalline cellulose (Prosolv SMCC 90) | 253.0 | 38.05 |
| Polyvinylpyrrolidone (PVP K-30) | 15.0 | 2.26 |
| Colloidal silicon dioxide | 5.0 | 0.75 |
| Talc | 5.0 | 0.75 |
| Magnesium stearate | 5.0 | 0.75 |
| Seal coat | | |
| Hydroxypropyl methylcellulose (HPMC 5 cps) | 20.49 | Coated to a weight gain of about 3% by weight of the core |
| Subcoat | | |
| Alginic acid | 60.39 | Coated to a weight gain of about 20% by weight of the seal coated core |
| Sodium bicarbonate | 12.08 | |
| Sodium starch glycolate | 30.20 | |
| Mannitol SD 25 | 15.10 | |
| Polyvinylpyrrolidone (PVP K-90F) | 18.12 | |
| Talc | 3.62 | |
| Tween 20 | 1.21 | |
| Outer coat | | |
| Noveon AA1 | 4.00 | Coated to a weight gain of about 12% by weight of the core with the seal coat and the subcoat |
| Sodium bicarbonate | 8.00 | |
| Eudragit L-100-55 | 31.99 | |
| Eudragit S-100 | 8.00 | |
| Mannitol SD 25 | 31.99 | |
| Sodium starch glycolate | 9.33 | |
| Tween 20 | 0.53 | |
| Polyethylene glycol (PEG 400) | 1.33 | |
| Talc | 2.13 | |
| Diethyl phthalate | 4.00 | |
| Top Coat | | |
| Baclofen | 7.5 | Coated to a weight gain of about 1.2% by weight of the coated core |
| Polyvinylpyrrolidone (PVP K-30) | 1.50 | |
| Talc | 2.25 | |
| Tween 20 | 0.40 | |

The coated tablets were obtained as mentioned in examples above. The core coated with the subcoat was placed in 100 mil of 0.01 N HCl and pH 4.5 buffer. It was found that the subcoated tablets remained at the base of the vessel and began to disintegrate after about 3 minutes, and fully disintegrated in about 6 minutes.

The subcoated cores were coated with the outer coat and placed in 100 ml of 0.01 N HCl and pH 4.5 buffer. The tablets were evaluated as regards the time required to float, i.e. buoyancy time, and the swelling index, i.e. increase in volume of the dosage form. The results are recorded in Table 26 below.

TABLE 26

| Medium used | Buoyancy time (minutes) | Swelling index | | | |
|---|---|---|---|---|---|
| | | 30 min | 120 min | 180 min | 210 min |
| 0.01N HCl | 9 | ~2.44 | ~3.50 | ~3.82 | ~4.20 |
| pH 4.5 buffer | 9 | ~3.08 | ~4.93 | ~5.25 | ~6.77 |

While the invention has been described by reference to specific embodiments, this was done for purposes of illustration only and should not be construed to limit the spirit or the scope of the invention.

The invention claimed is:

1. A gastric retention system which is a coated tablet comprising:
   (a) a core which is a tablet comprising an agent capable of generating internal pressure on the coat, wherein the agent capable of generating internal pressure is selected from the group consisting of gas generating agents and superdisintegrants, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof, and
   (b) an expandable coating formed by applying a coating composition comprising a film-forming polymer present in the range of 20 to 70% by weight of the expandable coating and one or more expandable components present in the range of 10 to 35% by weight of the expandable coating on the tablet core to form a film capable of expanding and maintaining its physical integrity in the gastric milieu, wherein the expandable component is selected from the group consisting of gas generating agents highly swellable polymers, superdisintegrants and mixtures thereof, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof and the highly swellable polymers are selected from alginates, carrageenan, hydroxypropyl guar, cross-linked polymer of acrylic acid or mixture thereof, and
   wherein said coated tablet is gastric retentive.

2. A gastric retention system comprising a gastric retention system as claimed in claim 1 and one or more therapeutically active agents.

3. A gastric retention system as claimed in claim 2 wherein one or more therapeutically active agents is present in an immediate release form and/or in a modified release form to provide an immediately releasing dose of one or more of the therapeutically active agents, and/or a modified release dose of the same or different therapeutically active agent(s).

4. A gastric retention system as claimed in claim 3 wherein the system has a floatation time of less than 15 minutes, when placed in an aqueous medium.

5. A gastric retention system which is a coated tablet comprising:
   (a) a core which is a tablet comprising an agent capable of generating internal pressure on the coat wherein the agent capable of generating internal pressure is selected from the group consisting of gas generating agents and superdisintegrants, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof,
   (b) a first coating comprising an agent capable of generating internal pressure on the coat, wherein the agent capable of generating internal pressure is selected from the group consisting of gas generating agents, highly swellable polymers, superdisintegrants and mixtures thereof and
   (c) a second coating formed by applying a coating composition comprising a film-forming polymer present in the range of 20 to 70% by weight of the expandable coating and one or more expandable components present in the range of 10 to 35% by weight of the expandable coating on the first coating whereby the second coating forms a film capable of expanding and maintaining its physical integrity in the gastric milieu, wherein the expandable component is selected from the group consisting of gas generating agents, highly swellable polymers, superdisintegrants and mixtures thereof, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof and the highly swellable polymers are selected from alginates, carrageenan, hydroxypropyl guar, cross-linked polymer of acrylic acid or mixture thereof, and
   wherein said coated tablet is gastric retentive.

6. A gastric retention system comprising a gastric retention system as claimed in claim 5 and one or more therapeutically active agents.

7. A gastric retention system which is a coated capsule, comprising:
   (a) a core which is a capsule, the core comprising an agent capable of generating internal pressure on the coating, wherein the agent capable of generating internal pressure is selected from the group consisting of gas generating agents and superdisintegrants, and wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof,
   (b) an expandable coating formed by applying a coating composition comprising a film-forming polymer present in the range of 20 to 70% by weight of the expandable coating and one or more expandable components present in the range of 10 to 35% by weight of the expandable coating, on the capsule core to form a film capable of expanding and maintaining its physical integrity in the gastric mileu, wherein the expandable component is selected from the group consisting of gas generating agents, highly swellable polymers, superdisintegrants and mixtures thereof, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof, and the highly swellable polymers are selected from alginates, carrageenan, hydroxypropyl guar, cross-linked polymer of acrylic acid or mixture thereof, and wherein said coated capsule is gastric retentive.

8. A gastric retention system comprising a gastric retention system as claimed in claim 7 and one or more therapeutically active agents.

9. A gastric retention system as claimed in claim 8 wherein one or more therapeutically active agents is present in an immediate release form and/or in a modified release form to provide an immediately releasing dose of one or more of the therapeutically active agents, and/or a modified release dose of the same or different therapeutically active agent(s).

10. A gastric retention system as claimed in claim 8, wherein the system is capable of instantaneously floating, when placed in an aqueous medium.

11. A gastric retention system which is a coated capsule comprising:
    (a) a core which is a capsule comprising an agent capable of generating internal pressure on the coat, wherein the agent capable of generating internal pressure is selected from the group consisting of gas generating agents and superdisintegrants, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof,
    (b) a first coating comprising an agent capable of generating internal pressure on the coat, wherein the agent capable of generating internal pressure is selected from the group consisting of gas generating agents, highly swellable polymers, superdisintegrants and mixtures thereof, and
    (c) a second coating formed by applying a coating composition comprising a film-forming polymer present in the range of 20 to 70% by weight of the expandable coating and one or more expandable components present in the range of 10 to 35% by weight of the expandable coating, on the first coating whereby the second coating forms a film capable of expanding and maintaining its physical integrity in the gastric milieu, wherein the expandable component is selected from the group consisting of gas generating agents, highly swellable polymers, superdisintegrants and mixtures thereof, wherein the gas generating agent is selected from the group consisting of carbonates, bicarbonates, sulfites, ammonium cations, sodium azide and mixtures thereof and wherein the superdisintegrants are selected from the group consisting of crosslinked sodium carboxymethyl cellulose, crosslinked polyvinylpyrrolidone, sodium starch glycolate, ion exchange resins and mixtures thereof and the highly swellable polymers are selected from alginates, carrageenan, hydroxypropyl guar, cross-linked polymer of acrylic acid or mixture thereof, and wherein said coated capsule is gastric retentive.

12. A gastric retention system as in claim 1, wherein the agent capable of generating internal pressure further comprises a highly swellable polymer.

* * * * *